(12) United States Patent
Allmendinger (10) Patent No.: US 10,561,390 B2
(45) Date of Patent: Feb. 18, 2020

(54) DOSE-REDUCED CT SCAN USING DYNAMIC COLLIMATION

(71) Applicant: Siemens Aktiengesellschaft, Munich (DE)

(72) Inventor: Thomas Allmendinger, Forchheim (DE)

(73) Assignee: SIEMENS AKTIENGESELLSCHAFT, Munich (DE)

( * ) Notice: Subject to any disclaimer, the term of this patent is extended or adjusted under 35 U.S.C. 154(b) by 932 days.

(21) Appl. No.: 14/437,321

(22) PCT Filed: Oct. 11, 2013

(86) PCT No.: PCT/EP2013/071249
§ 371 (c)(1),
(2) Date: Apr. 21, 2015

(87) PCT Pub. No.: WO2014/072153
PCT Pub. Date: May 15, 2014

(65) Prior Publication Data
US 2015/0272532 A1 Oct. 1, 2015

(30) Foreign Application Priority Data

Nov. 8, 2012 (DE) .................. 10 2012 220 313
Feb. 15, 2013 (DE) .................. 10 2013 202 491

(51) Int. Cl.
*A61B 6/00* (2006.01)
*A61B 5/0245* (2006.01)
(Continued)

(52) U.S. Cl.
CPC ............ *A61B 6/541* (2013.01); *A61B 5/0245* (2013.01); *A61B 5/0456* (2013.01); *A61B 6/032* (2013.01);
(Continued)

(58) Field of Classification Search
CPC ......... A61B 6/032; A61B 6/035; A61B 6/503; A61B 6/541; A61B 6/547
See application file for complete search history.

(56) References Cited

U.S. PATENT DOCUMENTS 6,434,215 B1 * 8/2002 Cesmeli ................. A61B 6/032
378/20
6,466,640 B1 10/2002 Taguchi
(Continued)

FOREIGN PATENT DOCUMENTS

CN 1846620 A 10/2006
CN 102397079 A 4/2012
(Continued)

OTHER PUBLICATIONS

International Search Report PCT/ISA/210 for International Application No. PCT/ dated Dec. 17, 2013.
(Continued)

*Primary Examiner* — Amanda Lauritzen Moher
*Assistant Examiner* — Katherine M McDonald
(74) *Attorney, Agent, or Firm* — Harness, Dickey & Pierce, P.L.C.

(57) ABSTRACT

A computer tomograph, a method, and a computer program product are disclosed. A computer tomograph is disclosed for scanning an image of at least one examination region of a patient, including a scanning unit which can be rotated about a longitudinal axis. The scanning unit includes an X-ray detector and an X-ray emitter. The extension of an X-ray beam emitted by the X-ray emitter is controlled for scanning purposes along the longitudinal axis using at least one patient-dependent control signal. By controlling the extension of the X-ray beam, the dose applied to the patient is also controlled such that the dose can be used as efficiently as possible. The control further allows the pitch to be (Continued)

matched to the patient-dependent control signal while scanning in the spiral mode.

20 Claims, 3 Drawing Sheets

(51) Int. Cl.
    *A61B 5/0456*     (2006.01)
    *A61B 6/03*     (2006.01)
    *A61B 6/04*     (2006.01)

(52) U.S. Cl.
    CPC ............ *A61B 6/0407* (2013.01); *A61B 6/542* (2013.01); *A61B 6/547* (2013.01)

(56) References Cited

U.S. PATENT DOCUMENTS

| | | | |
|---|---|---|---|
| 7,260,171 B1 | 8/2007 | Arenson et al. | |
| 7,515,678 B2 * | 4/2009 | Hsieh | A61B 6/032 250/370.09 |
| 2003/0036693 A1 * | 2/2003 | Avinash | A61B 5/055 600/413 |
| 2004/0120450 A1 | 6/2004 | Flohr et al. | |
| 2005/0249328 A1 | 11/2005 | Bruder et al. | |
| 2006/0177002 A1 | 8/2006 | Toth et al. | |
| 2006/0274878 A1 | 12/2006 | Hsieh et al. | |
| 2010/0091937 A1 | 4/2010 | Raupach et al. | |
| 2011/0004112 A1 * | 1/2011 | Flohr | A61B 5/0456 600/522 |
| 2012/0082291 A1 | 4/2012 | Allmendinger et al. | |

FOREIGN PATENT DOCUMENTS

| | | |
|---|---|---|
| DE | 10245943 A1 | 4/2004 |
| DE | 102004021965 A1 | 12/2005 |
| DE | 102007053390 A1 | 12/2008 |
| DE | 102008049087 A1 | 4/2010 |
| DE | 102008049708 A1 | 4/2010 |
| DE | 102009034054 A1 | 8/2010 |
| DE | 102010041781 A1 | 4/2012 |
| WO | WO-2009141766 A2 | 11/2009 |

OTHER PUBLICATIONS

Written Opinion of the International Searching Authority PCT/ISA/237 for International Application No. PCT/ dated Dec. 17, 2013.

Chinese Office Action and English translation thereof dated Dec. 26, 2016.

Chinese Office Action and English translation thereof dated Jun. 13, 2018.

\* cited by examiner

DOSE-REDUCED CT SCAN USING DYNAMIC COLLIMATION

PRIORITY STATEMENT

This application is the national phase under 35 U.S.C. § 371 of PCT International Application No. PCT/EP2013/071249 which has an International filing date of Oct. 11, 2013, which designated the United States of America, and which claims priority to German patent application number DE 102013202491.6 filed Feb. 15, 2013 and German patent application number DE 102012220313.3 filed Nov. 8, 2012, the entire contents of each of which are hereby incorporated herein by reference.

FIELD

At least one embodiment of the invention generally relates to an apparatus and to a method for recording an image and also to a computer program product.

BACKGROUND

X-ray based computed tomography, abbreviated to CT, is an established method of three-dimensional imaging, especially for diagnostic purposes. CT not only makes possible spatially high-resolution imaging, but also allows, by way of a timed series of recordings, especially with administration of contrast medium, detailed conclusions to be drawn about the function of organs, for example the heart and the surrounding coronary vessels. In order to optimize the conditions for a CT recording as well as reconstruction of such recordings, regular patient-dependent information is needed. Such information is obtained for example from an electrocardiogram, abbreviated to EKG. Basically a dose which is as low as possible must be ensured for the patient in order to prevent damage from x-ray radiation. Therefore patient-dependent information is needed, especially for reduction of the applied dose. The dose is understood as the energy dose for example, i.e. the energy of the x-ray radiation that a patient absorbs per kg of body weight; the Gray unit is used for a dose defined in this way. A dose can also be understood as the effective dose in Sievert units.

Patent DE 102 45 943 B4 discloses a method and a CT device for creating CT images of an organ which moves periodically. The patent relates to the creation of CT images of a periodically moving organ of a living being, wherein the organ has areas with rest and movement phases and the rest phases of different areas of the organ occur at different points in time, by way of a CT device with an x-ray radiation source moved around the body of the living being to be examined for creating the CT images. First of all a plurality of projections for the purposes of image creation is recorded during at least one orbit of the x-ray radiation source around the object to be examined and a period of time, which is at least equal to a period of the movement, is recorded. Then the data corresponding to the projections is analyzed as to whether it was obtained during a rest or movement phase of a region of interest of the organ in each case. Then an image of the organ is reconstructed using only such data as was obtained during a rest phase of the respective region of interest. The analyzing of the data corresponding to the projections includes it being analyzed in relation to a number of regions of interest of the organ as to whether a rest or a movement phase of the respective area was obtained, wherein, in relation to all regions of interest of the organ, in each case an image of the organ is reconstructed using only such data as has been obtained during a rest phase of the respective region of interest of the organ, and wherein an image comprising all regions of interest of the organ in their respective rest phase is created from the images representing the rest phase of the individual regions of interest of the organ. With the CT images necessarily reconstructed in different heart phases an overall diagnosis for all vessels on the basis of the images showing the individual vessels in their rest phase is possible. The heart signals are used for an improved reconstruction, but the method does not directly reduce the applied dose. A signal representing a threshold criterion for the physiological function can actually be predetermined which, when fulfilled, is a region of interest of the organ in a rest phase in each case. To record the projections necessary for creating an image the x-ray radiation source is only activated during those time segments during which the threshold criterion is fulfilled. This method can be realized as EKG-triggered dose modulation and lowers the applied dose directly. However the projections recorded then no longer allow a reconstruction in each phase of the heart cycle, since only projections from the rest phase are available.

SUMMARY

At least one embodiment of the invention includes efficiently using the applied dose during a CT recording of an examination area, especially for a recording in spiral mode.

A computed tomograph, a method and a computer program product are disclosed.

At least one embodiment of the invention is described below in relation to the claimed apparatus and also in relation to the claimed method. Features, advantages or alternate forms of embodiment mentioned here are likewise to be transferred to the other claimed subject matter and vice versa. In other words the physical claims which are directed to an apparatus for example can also be developed with the features which are described or claimed in conjunction with a method. The corresponding functional features of the method are embodied in such cases by corresponding physical modules.

At least one embodiment of the invention is based on a computed tomograph for recording an image of at least one examination area of the patient, comprising a recording unit able to be rotated about a longitudinal axis, wherein the recording unit comprises an x-ray detector and also an x-ray emitter. The idea underlying the invention is to control the extension of an x-ray beam emitted by the x-ray emitter along the longitudinal axis by way of at least one patient-dependent control signal. This idea can be realized both in the form of at least one embodiment of the inventive computed tomograph and also in the form of at least one embodiment of the inventive method. Through the control of the extension of the x-ray beam the applied dose of the patient is also controlled, allowing the most efficient possible usage of the dose. The control also makes it possible, during a recording in spiral mode, to adapt the pitch to the patient-dependent control signal and thus to make the most efficient use possible of the applied dose. The pitch is adapted in accordance with the invention by the control of the extension of the x-ray beam causing an adaptation of the illuminated surface of the x-ray detector.

In accordance with a further aspect of at least one embodiment, the inventive method comprises the recording of a contrast medium-supported image. This means that at least one of the inventive advantages come into play especially for the especially important recordings of contrast medium-supported images in medical diagnostics.

At least one embodiment of the invention further comprises a computer program product which is able to be loaded directly into a processor of a programmable computer, with program code segments for executing at least one embodiment of the inventive method when the program product is executed on a computer. This enables the method to be executed quickly, with identical repetitions and robustly.

BRIEF DESCRIPTION OF THE DRAWINGS

In the figures.

DETAILED DESCRIPTION OF EXAMPLE EMBODIMENTS

At least one embodiment of the invention is based on a computed tomograph for recording an image of at least one examination area of the patient, comprising a recording unit able to be rotated about a longitudinal axis, wherein the recording unit comprises an x-ray detector and also an x-ray emitter. The idea underlying the invention is to control the extension of an x-ray beam emitted by the x-ray emitter along the longitudinal axis by way of at least one patient-dependent control signal. This idea can be realized both in the form of at least one embodiment of the inventive computed tomograph and also in the form of at least one embodiment of the inventive method. Through the control of the extension of the x-ray beam the applied dose of the patient is also controlled, allowing the most efficient possible usage of the dose. The control also makes it possible, during a recording in spiral mode, to adapt the pitch to the patient-dependent control signal and thus to make the most efficient use possible of the applied dose. The pitch is adapted in accordance with the invention by the control of the extension of the x-ray beam causing an adaptation of the illuminated surface of the x-ray detector.

In accordance with a further aspect of at least one embodiment of the invention, the computed tomograph has a collimator for controlling the extension of the x-ray beam. The extension of the x-ray beam is controlled very quickly and precisely by way of a collimator.

In accordance with a further aspect of at least one embodiment of the invention, the computed tomograph has a patient couch, wherein the patient couch is designed to move with a defined velocity of advance during the recording of the image. The defined velocity of advance enables a spiral recording of the examination area to be realized in an especially simple and robust manner, of which the pitch is controlled by the extension of the x-ray beam.

In accordance with a further aspect of at least one embodiment of the invention, the computed tomograph is designed to control the extension of the x-ray beam as a function of changing values of the control signal during the recording or between at least two recordings. Such dynamic control of the extension ensures that during a recording or between at least two recordings the correct extension of the x-ray beam is selected. Through this the dose is used especially efficiently.

In accordance with a further aspect of at least one embodiment of the invention, the computed tomograph is designed to control the extension of the x-ray beam as a function of a value of the control signal predicted from the measured values of the control signal. This enables the extension of the x-ray beam to be adapted especially well to the control signal and in this way is a condition of an especially efficient use of the dose.

In accordance with a further aspect of at least one embodiment of the invention, the examination area comprises the heart of the patient, wherein the control signal comprises a control signal derived from the heart frequency of the patient. The advantages of at least one embodiment of the invention thus also extend to the recording of the heart.

At least one embodiment of the invention also includes the control signal being determined with reference to an EKG signal, through which an especially precise determination of the control signal and thereby an especially precise control is made possible.

In accordance with a further aspect of at least one embodiment of the invention, the extension of the x-ray beam is controlled immediately after an R wave in the EKG signal. This is because the time directly after an R wave is not generally of significance for the reconstruction of an image of the heart. This means that the greatest possible range of the heart cycle which is suitable for the reconstruction of an image remains.

In accordance with a further aspect of at least one embodiment of the invention, the control signal comprises a control signal derived from the x-ray absorption of the examination area, which enables the control signal to be determined directly from an image of the examination area recorded by way of the inventive computed tomograph.

In accordance with a further aspect of at least one embodiment, the inventive method comprises the recording of a contrast medium-supported image. This means that at least one of the inventive advantages come into play especially for the especially important recordings of contrast medium-supported images in medical diagnostics.

At least one embodiment of the invention further comprises a computer program product which is able to be loaded directly into a processor of a programmable computer, with program code segments for executing at least one embodiment of the inventive method when the program product is executed on a computer. This enables the method to be executed quickly, with identical repetitions and robustly.

Figure 1:
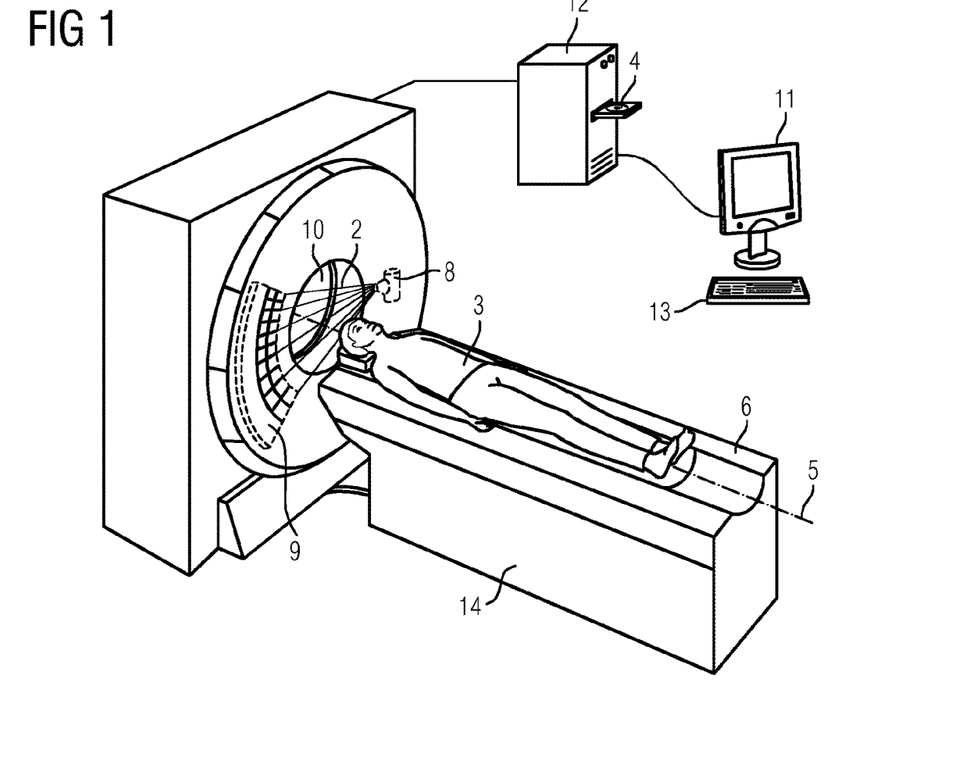
FIG. 1 shows an inventive computed tomograph.

FIG. 1 shows an embodiment of an inventive computed tomograph having a recording unit, comprising an x-ray emitter 8 and also an x-ray detector 9. The recording unit rotates during a recording about a longitudinal axis 5 and the x-ray emitter 8 emits x-ray radiation during the recording in the form of an x-ray beam 2 which possesses an extension along the longitudinal axis 5 and also an extension along the long side of the x-ray detector 9 oriented at right angles to the longitudinal axis 5. The x-ray beam 2 is thus embodied in the shape of a pyramid. In this application, unless otherwise specified, an extension of an x-ray beam 2 means the extension of the x-ray beam 2 along the longitudinal axis 5. The computed tomograph can also have more than just one x-ray emitter 8 and more than just one x-ray detector 9, especially to make possible recordings in so called dual-energy methods. The x-ray emitter 8, in the example shown here involves an x-ray tube. The x-ray detector 9, in the example shown here, involves a row detector with a number of rows. The x-ray detector 9 can further also be embodied as a flat-panel detector. The x-ray detector 9 is usually embodied as a scintillator counter, in which the high-energy x-ray photons are converted by way of a scintillator into lower-energy photons in the optical spectrum and are subsequently detected by way of a photodiode. As an alternative the x-ray detector 9 can be embodied as a direct-converting detector, which converts the high-energy x-ray photons by way of the semiconductor material directly, by internal photoexcitation utilizing the photovoltaic principle, into a stream of electrical signals.

During the recording of the image the patient 3 lies on a patient couch 6, which is connected to a couch pedestal 14 such that it bears the patient couch 6 with the patient 3. The patient couch 6 is designed to move the patient 3 in a recording direction through the opening 10 of the recording unit. The recording direction is generally specified by the longitudinal axis 5 about which the recording unit rotates during a recording. However the longitudinal axis 5 can also be tilted in relation to the recording direction along which the patient 3 is moved during the recording, for example by the recording unit being embodied as part of a tiltable gantry.

The x-rays of the x-ray beam 2 are attenuated by the patient 3 during a recording and are detected by the x-ray detector 9 so that an x-ray projection of the respective recording area 15 is produced. Through the rotation of the recording unit x-ray projections are recorded from different directions which can be reconstructed to form a high-resolution, spatially three-dimensional image. In this case the recording area 15 includes at least one examination area of the patient 3. An examination area can in principle involve any given parts of the body or organs of a patient 3, for example their head, thorax, abdomen or brain, heart, coronary vessels, kidney, liver etc.

In the sense of the present application, recording an image, especially of an examination area, can mean both the recording of an individual x-ray projection and also the recording of a number of x-ray projections which are suitable for reconstructing a high-resolution, spatially three-dimensional image of the respective examination area. An image below means an x-ray image in the form of an x-ray image reconstructed from at least one x-ray projection. In particular an image can involve a spatially three-dimensional image and also a slice image.

The recording can especially involve a contrast medium-supported recording. A contrast medium-supported recording is to be understood as the recording of an image of which the contrast is based at least partly on a contrast medium. Contrast medium is generally defined as such media as improve the presentation of structures and functions of the body in the imaging methods. Within the context of the present invention contrast media are to be understood both as conventional contrast media, such as iodine for example, and also as tracers such as 18F, 11C or 13N for example.

In accordance with an embodiment of the invention, the recording is made in the spiral mode. In the spiral mode the patient 3 is moved continuously during the recording of x-ray projections. In the spiral mode the pitch p is defined as the ratio of velocity of advance of the patient couch 6 per rotation of the recording unit to the extension of the x-ray beam 2 along the longitudinal axis 5. For a velocity of advance v of the patient couch 6, a rotation time T_rot of the recording unit, a slice thickness S of a row of the x-ray detector 9, for which N rows are illuminated, the following general equation applies:

$$p = v \cdot T\_\mathrm{rot}/(N \cdot S)$$

The selection of the pitch depends on a number of factors. If a patient 3 in their abdomen as examination area, for example as a result of fatty deposits, has an especially high x-ray absorption, then the pitch for this area should be selected as a small number, especially p<1. If with a single spiral recording a second examination area is also to be recorded with a lower x-ray absorption, for example the thorax, then it is worth making the effort of modifying the pitch during the recording. This is because, as a result of the higher x-ray absorption of the abdomen in relation to the thorax, a lower pitch should be selected during the recording of the abdomen than during the recording of the thorax. Further examples of examination areas which often have a different level of x-ray absorption and which are further regularly recorded with a single spiral recording are head/neck and also pelvis/legs.

Depending on the underlying problem it is desirable to record different examination areas of the patient 3 in spiral mode with a different dose or different pitch. An embodiment of the present invention then has advantages especially if dose modulation is not desired or—beyond certain limits—is not possible, for example because the current for the voltage of the x-ray tubes cannot be set beyond a certain limit value. The present invention then provides an especially efficient option of regulating the dose and does so by regulating the pitch during the recording by way of controlling the extension of the x-ray beam 2. Such regulation also makes possible a constant velocity of advance of the patient couch 6 which is desirable for a patient-friendly sequence of the recording procedure.

A pitch which is selected as too small does not have a negative effect on the reconstruction but brings with it an increased dose and an increased recording duration. The applied dose can thus be used more efficiently if a high pitch is selected, taking into consideration the boundary conditions for a reconstruction of the examination area or of the recording area 15. The invention makes use of this knowledge by adapting the pitch to a patient-dependent control signal through control of the extension of the x-ray beam 2.

In accordance with an embodiment of the invention, the computed tomograph is designed to control the extension of an x-ray beam 2 emitted by the x-ray emitter 8 for recording by way of a patient-dependent control signal. Through the control of the extension of the x-ray beam 2 the applied dose for the patient 3 is also controlled. Since the control makes it possible to adapt the pitch to the control signal during a recording in spiral mode, the applied dose can be used as efficiently as possible with an embodiment of the invention.

The control signal involves a signal, typically a digital signal, derived from a bodily, especially physiological, characteristic of the patient 3. The control signal can also be derived from a characteristic of the examination area, especially from the part of the examination area just irradiated by the x-ray source 8.

The bodily characteristic of the patient 3 involves the x-ray absorption of the examination area for example. Such x-ray absorption can especially be obtained from a previously recorded topogram of the examination area. Furthermore automatic detection of a predeterminable examination area in the topogram can be embodied as part of the invention. The recording and evaluation of a topogram also allow the position of the patient 3 and thus of the examination area relative to the patient couch 6 to be determined. The control signal can in this way be made directly dependent on the position of the patient couch 6.

The bodily characteristic can also involve the characteristic of an organ, which is determined for example by way of a contrast medium-supported image. Furthermore the bodily characteristic can involve metabolism characteristics of an organ or of another examination area, for the determination of which contrast media, especially tracers, are regularly used.

In a further form of embodiment, the computed tomograph is designed to control the extension of the x-ray beam 2 along the longitudinal axis 5 as a function of changing values of the control signal during the recording between at least two recordings.

In a further form of embodiment, the patient couch 6 is designed to move at a defined velocity of advance during the recording of the examination area of a patient 3 lying on the patient couch 6. The defined velocity of advance enables a spiral recording of the examination area to be controlled in an especially simple and robust manner, of which the pitch is controlled by the extension of the x-ray beam 2.

Furthermore the extension of the x-ray beam 2 is controlled in a form of embodiment of the invention with a diaphragm, which is also referred to as a collimator. Such a collimator is as a rule attached directly after the beam outlet of the x-ray emitter 8 and is embodied to restrict the x-ray beam 2 both in its extension along the longitudinal axis 5 and also along the long side of the x-ray detector 9 oriented at right angles to the longitudinal axis 5. Such a collimator is shown by way of example and schematically in FIG. 3 and FIG. 4.

Figure 3:
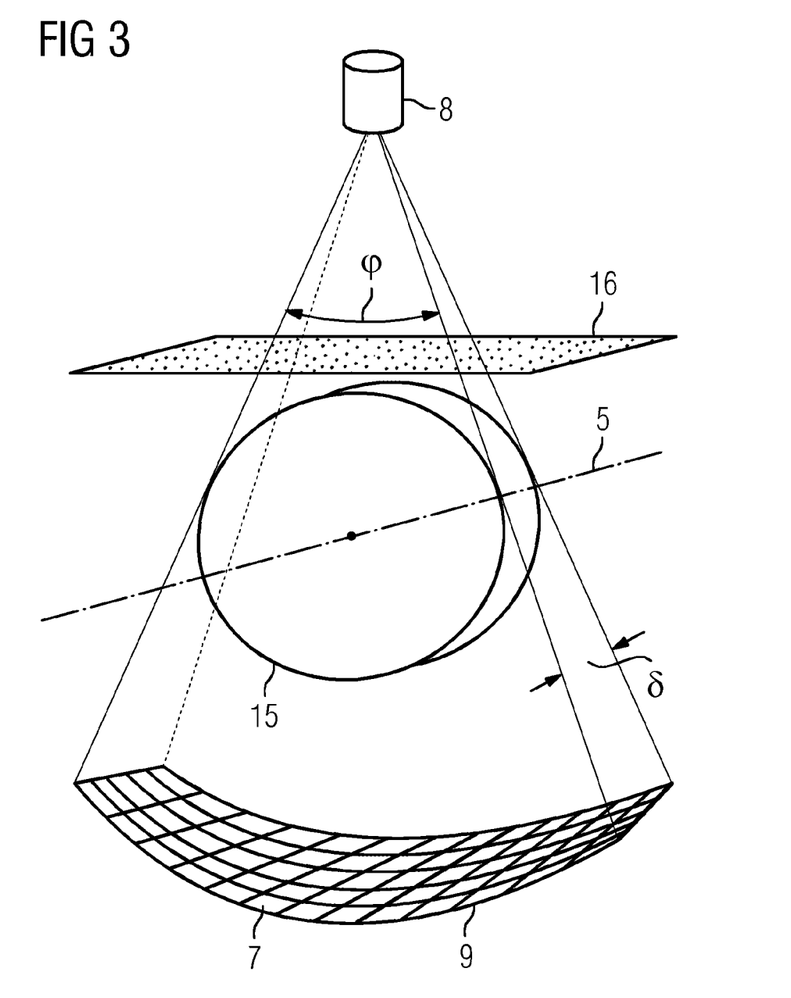
FIG. 3 shows a schematic diagram of the recording geometry of an embodiment of an inventive computed tomograph.
Figure 4:
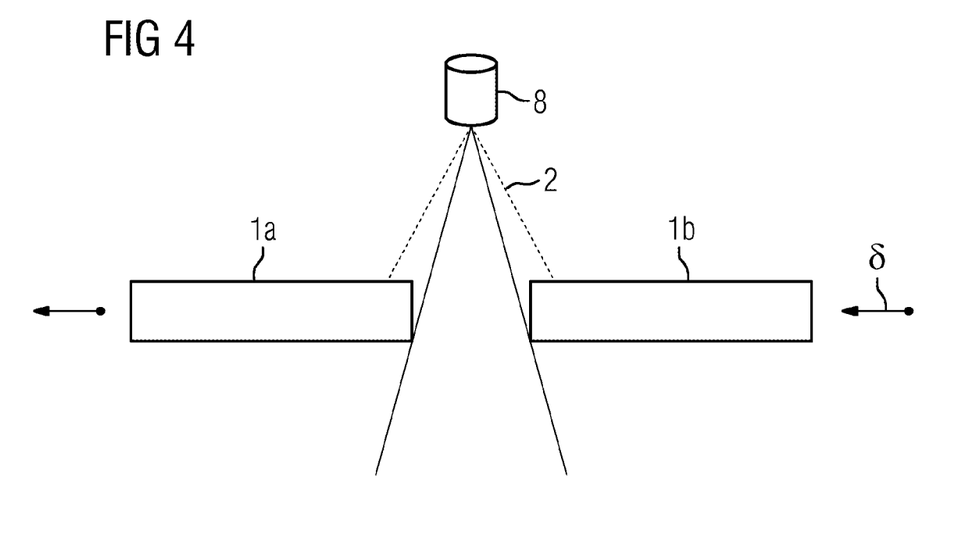
FIG. 4 shows a schematic diagram of a collimator.

The extension of the x-ray beam 2 is controlled especially quickly and reliably by way of a collimator, since such a collimator only has a small mass and thus a low inertia. A modern collimator achieves an acceleration of $2 \text{ m·s}^2$ as well as a speed of $0.2 \text{ m·s}^{-1}$. For example with a control that 96 instead of 72 rows must be illuminated by the x-ray beam 2, the individual collimator elements 1a, 1b with a symmetrical arrangement must each move by 3 mm. Such movement is completed within 80 ms, which with a typical duration of a heart cycle of 1 second means that the movement of the diaphragm can be completed in less than 10% of the time of a heart cycle.

The computer 12 is connected to an output unit 11 and also to an input unit 13. The output unit 11 involves one (or more) LCD, plasma or OLED screen(s) for example. The output on the output unit 11 involves a graphical user interface for example for manual entry of patient data as well as for activation of the individual units of the computer tomograph and for input and selection of recording parameters. The input unit 13 involves a keyboard, a mouse, a touchscreen or also a microphone for voice input for example.

An embodiment of the invention further comprises a computer program product which is able to be loaded directly into a processor of a programmable computer 12, with program code segments to execute an embodiment of the inventive method when the computer program is executed in a computer 12. The computer program product is configured so that it can execute an embodiment of the inventive method steps by way of the computer 12. The computer 12 in this case must have the respective prerequisites such as a corresponding main memory, a corresponding graphics card or a corresponding logic unit for example, so that the respective method steps can be executed efficiently. The computer program product is stored for example on a computer-readable medium 4 or is held on a network or server, from where it can be loaded into the processor of a local computer 12 which is directly connected to the computed tomograph or is embodied as part of the computed tomograph.

A further example of the use of an embodiment of the present invention is a recording of the heart, which performs a number of heart cycles as a rule during a spiral recording. In this application example the control signal is derived from the heart frequency of the patient 3; a control signal derived from the heart frequency of the patient 3 is also referred to below as the heart frequency signal. Directly consecutive recordings of the heart are usual in contrast medium-supported examinations, in order to achieve a more high-contrast presentation of the heart and of the coronary vessels. The pitch must be selected in this case so that even with a fluctuation of the value of the heart frequency, each position of the heart along the longitudinal axis 5 can be sampled during each phase of the heart cycle. It follows from this that a lower value of the heart frequency requires a smaller pitch. Therefore, in conventional spiral mode the pitch must be oriented to the lowest anticipated value of the heart frequency during a recording. The lowest value of the heart frequency is anticipated for example by the lowest value of the heart frequency being selected from ten heart cycles measured directly before the recording and in addition a correction value of eight beats per minute being subtracted from the selected value of the heart frequency. This means that although the pitch is dependent on the heart frequency, as a rule the velocity of advance of the patient couch 6 is set in such cases and this is done only once before the beginning of a recording or of a series of recordings.

An embodiment of the invention allows the pitch for a recording of the heart to no longer have to be oriented to the lowest anticipated value of the heart frequency. Instead the recording can be started for example with a pitch which is based on the average value H_av with the heart frequency of three heart cycles directly before the recording. In this case the extension of the x-ray beam 2 along the longitudinal axis 5 is set in a form of embodiment so that the x-ray beam 2 only illuminates 75% of the extent of the x-ray detector 9 along the longitudinal axis 5. Thus, with a multi-row x-ray detector 9, only a part of all rows available is illuminated by the x-ray beam 2, for example 72 rows for a 96-row x-ray detector 9. This means that sufficient room for maneuver is available to increase the extension of the illuminated area of the x-ray detector 9 along the longitudinal axis 5. If the value of the heart frequency now reduces during the recording then the pitch can be reduced by way of an increased extension of the x-ray beam 2 along the longitudinal axis 5 (and vice versa). For a value H of the heart frequency, for the number N of the rows of a multi-row x-ray detector 9 illuminated in accordance with the invention by the x-ray beam 2, the following applies:

$$N(H)=(H\_av/H)+\alpha \cdot T\_\text{rot},$$

wherein $\alpha$ is the reconstruction angle and T_rot is usefully specified in units of m/(s angle). The reconstruction angle $\alpha$ specifies the angular range in which projections of a point in the recording area are to be accepted. The minimum reconstruction angle $\alpha$ amounts to 180°.

In a form of embodiment of the invention, x-ray projections of the heart are recorded continuously as the examination area during the rotation of the recording unit, so that an image of the heart can basically be reconstructed in each phase of the heart cycle. As an alternative to this a recording of x-ray projections can be undertaken only in the rest phases of the heart cycle, since the rest phases are especially suitable for a reconstruction. In this case the control aims to adapt the pitch to the length of the rest phases of the heart cycle.

The measured values of the control signal for predicting the value of the control signal can also involve the current value of the heart frequency obtained from only one heart cycle or can involve a value derived from a series of heart cycles, for example an average value or an extreme value. The value of the control signal derived from the heart frequency of the patient 3 is transferred with the aid of a computer 12 for further processing to a control unit of the computed tomograph. Such a control unit can especially be designed for activating the collimator as well as the individual collimator elements 1a, 1b.

Such a temporally dynamic control of the extension of the x-ray beam 2 insures, for a recording of the heart, that during a recording or between at least two recordings the extension of the x-ray beam 2 correct for a given heart cycle is selected. The pitch is thus adapted in spiral mode as a function of changing values of a heart frequency signal, for example after each renewed heartbeat, by way of a control of the surface of the x-ray detector 9 illuminated by the x-ray beam 2 such that through this the applied dose is used especially efficiently. Furthermore the control can also be undertaken such that it is dependent on a predicted heart frequency signal, wherein the predicted heart frequency signal can especially involve a signal which corresponds to the length or frequency of the next heart cycle. Such a signal is for example then very easy to predict after an additional systole has occurred i.e. when a heart cycle was especially short. This is because the subsequent heart cycle is as a rule significantly longer in order to compensate for the previous additional systole.

Figure 2:
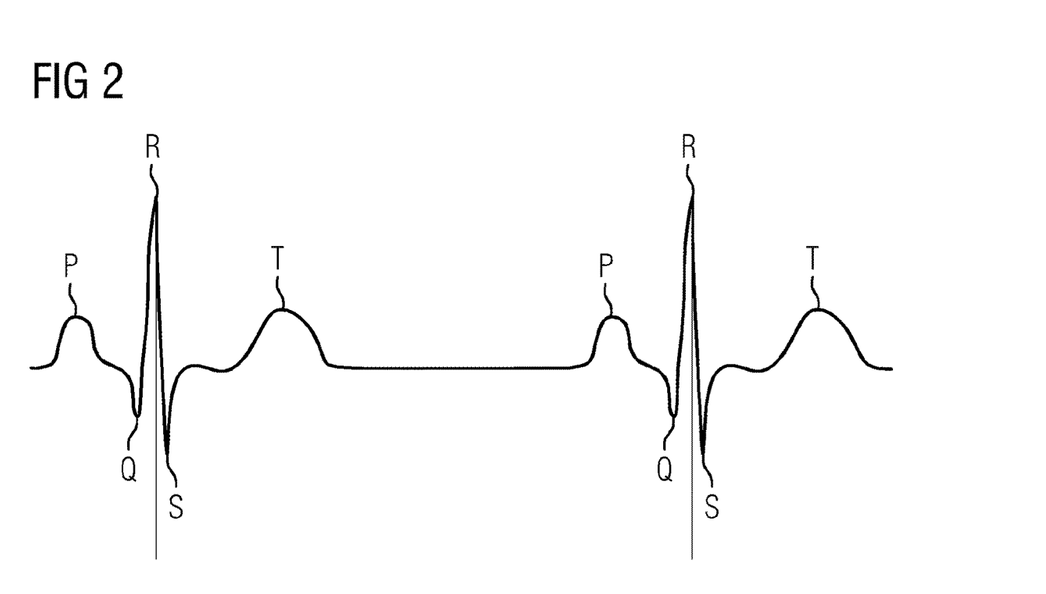
FIG. 2 shows the timing sequence of an EKG signal.

FIG. 2 shows the timing curve of an EKG signal, wherein the time progresses in the horizontal from left to right. An EKG records a summary of the electrical signals which stem from the activity of the heart muscle fibers. In such cases as a rule the voltage between two electrodes attached to the skin of the patient 3 is measured. The recording of an EKG of a patient 3 is generally done during a CT recording of the heart of the same patient 3. Therefore the EKG is a suitable device for determining heart frequency signals for controlling the extension of the x-ray beam 2.

The waves designated Q, R and S are also referred to as the QRS complex. Because of its striking form this offers a way of determining the heart frequency of a patient 3. For this the period between two repeating characteristic points in the EKG simply has to be measured. In particular the beat of the R wave R is suitable as such a characteristic point. Furthermore the area directly after the R wave R is especially well suited for undertaking control of the extension of the x-ray beam 2, for example by controlling a collimator positioned in front of the x-ray emitter 8. This is because the time directly after an R wave R is not as a rule of importance for the reconstruction of an image of the heart. This means that as large an area as possible of the heart cycle which is suitable for the reconstruction of image remains. This area is especially the rest phase of the heart between the characteristic peaks of the EKG signal identified by T and P.

FIG. 3 shows a schematic diagram of the recording geometry of the computed tomograph. The x-ray beam 2, which is embodied in the form of a pyramid, is emitted by an x-ray source 8 and is filtered or collimated spatially by a collimator which lies in a collimator plane 16. The remaining x-ray beam 2 then falls on a recording area 15, which at least partly absorbs the x-ray radiation of the x-ray beam 2. In a form of embodiment of an embodiment of the inventive method the recording area 15 comprises the heart of a patient 3 and the surrounding tissue. The transmitted x-ray radiation of the x-ray beam 2 then falls on the x-ray detector 9 and thus allows a recording of individual x-ray projections. X-ray emitter 8 and x-ray detector 9 are part of a recording unit, which rotate around a longitudinal axis 5 in order to make possible a recording of x-ray projections from different directions and thus a three-dimensional reconstruction of the recording area 15. The x-ray detector 9 consists of individual detector elements 7, which form rows which are disposed along the radial angular area φ. The angular area δ by contrast specifies the extension of the x-ray beam 2 along the longitudinal axis 5. The collimator is designed to restrict and to shape the x-ray beam 2 along the two angular areas φ and δ independently of one another. This is typically achieved by the collimator being constructed from material which absorbs x-ray radiation to a high degree. The displacement of individual collimator elements 1a, 1b into the area of the x-ray beam 2 emitted by the x-ray emitter 8 thus represents an option for controlling the extension of the x-ray beam 2 along the longitudinal axis 5. Furthermore the collimator elements 1a, 1b can naturally also be activated so that they can restrict and shape extension of the x-ray beam 2 along the long side of the x-ray detector 9 oriented at right angles to the longitudinal axis 5.

FIG. 4 shows a schematic diagram of a collimator. The two collimator elements 1a and 1b involve two blocks which consist of one material which absorbs x-ray radiation to a large extent, for example this material can contain tungsten, molybdenum, iron and other metals. Thus the x-ray radiation of the x-ray beam 2 emitted by the x-ray emitter 8, which strikes the collimator elements 1a and 1b, is so heavily absorbed that its intensity is greatly reduced on the opposite side. By contrast the central part of the x-ray beam 2 passes through the free area of the collimator with its intensity undiminished. The direction indicated by arrows along the angular area δ is oriented along the longitudinal axis 5. Basically however the direction indicated by arrows can also involve a direction along the radial angular area φ. This is because the collimator is designed to restrict and to shape the extension of the x-ray beam 2 in both directions. This can be done for example by a collimator in the shape of what is known as a multi-leaf collimator, as are known for example from radiation therapy.

Although the invention has been illustrated and described in greater detail by the preferred example embodiments, the invention is not restricted by the disclosed examples and other variations can be derived herefrom by the person skilled in the art, without departing from the scope of protection of the invention. In particular method steps can be performed in an order other than that specified.

What is claimed is:

1. A computed tomograph for recording an image of at least one examination area of a patient, comprising:
    a recording unit, rotatable about a longitudinal axis, the recording unit including an x-ray detector and an x-ray emitter, wherein the computed tomograph is configured to control a degree of an opening of a collimator to control an extension of an x-ray beam emitted for recording by the x-ray emitter, along the longitudinal axis, as a function of changing values of at least one patient-dependent control signal and the computed tomograph is configured to control the extension of the x-ray beam directed to the patient based on a value of the at least one patient-dependent control signal predicted from the changing values of the at least one patient-dependent control signal; and
    a patient couch, the patient couch being configured to move during the recording of the image with a denied velocity of advance.

2. The computed tomograph of claim 1, wherein the recording unit includes a collimator to control the extension of the x-ray beam.

3. The computed tomograph of claim 1, wherein the computed tomograph is configured to control the extension of the x-ray beam based on the changing values of the at least one patient-dependent control signal during the recording or between at least two recordings.

4. The computed tomograph of claim 1, wherein the examination area comprises a heart of the patient, and wherein the at least one patient-dependent control signal comprises a control signal derived from a heart frequency of the patient.

5. The computed tomograph of claim 4, wherein the computed tomograph is configured to determine the control signal based on an EKG signal of the heart.

6. The computed tomograph of claim 5, wherein the computed tomograph is configured to control the extension of the x-ray beam after an R wave in the EKG signal.

7. The computed tomograph of claim 1, wherein the control signal comprises a control signal derived from an x-ray absorption of the examination area.

8. A method for recording an image of at least one examination area of a patient via a computed tomograph including a recording unit rotatable about a longitudinal axis, the recording unit including an x-ray detector and an x-ray emitter, the method comprising:
controlling a degree of an opening of a collimator to control an extension of an x-ray beam emitted by the x-ray emitter for recording, along the longitudinal axis, using a function of changing values of at least one patient-dependent control signal and the extension of the x-ray beam directed to the patient is controlled based on a value of the at least one patient-dependent control signal predicted from the changing values of the at least one patient-dependent control signal; and
moving a patient couch with a defined velocity of advance during the recording.

9. The method of claim 8, wherein the recording unit includes a collimator for controlling the extension of the x-ray beam.

10. The method of claim 8, wherein the extension of the x-ray beam is controlled based on the changing values of the at least one patient-dependent control signal during the recording or between at least two recordings.

11. The method of claim 8, wherein the examination area comprises a heart of the patient and wherein the at least one patient-dependent control signal comprises a control signal derived from a heart frequency of the patient.

12. The method of claim 11, further comprising
determining the control signal based on an EKG signal of the heart.

13. The method of claim 12, wherein the extension of the x-ray beam is controlled after an R wave in the EKG signal.

14. The method of claim 8, further comprising
determining an x-ray absorption of the examination area, wherein the at least one patient-dependent control signal comprises a control signal derived from an x-ray absorption of the examination area.

15. The method of claim 8, wherein the recording comprises the recording of a contrast medium-supported image.

16. A non-transitory computer readable medium, when executed by a processor of a computed tomograph, configured to cause the computed tomograph to execute the method of claim 8.

17. The method of claim 9, wherein the examination area comprises a heart of the patient and wherein the at least one patient-dependent control signal comprises a control signal derived from a heart frequency of the patient.

18. The method as claimed in claim 17, further comprising determining the control signal based on an EKG signal of the heart.

19. The computed tomograph of claim 1, wherein the at least one patient-dependent control signal is a signal derived from a heart frequency of the patient and the computed tomograph is configured to control the extension of the x-ray beam based on an average of the heart frequency.

20. The computed tomograph of claim 1, wherein the computed tomograph is configured to control the degree of the opening of the collimator as a function of changing values of the at least one patient-dependent control signal that occur during the recording.

* * * * *